United States Patent
Maruta

(10) Patent No.: US 10,251,616 B2
(45) Date of Patent: Apr. 9, 2019

(54) RADIOGRAPHIC IMAGE CAPTURING APPARATUS AND RADIOGRAPHIC IMAGE CAPTURING SYSTEM

(71) Applicant: Konica Minolta, Inc., Chiyoda-ku, Tokyo (JP)

(72) Inventor: Yuuichi Maruta, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/615,125

(22) Filed: Jun. 6, 2017

(65) Prior Publication Data
US 2017/0347984 A1    Dec. 7, 2017

(30) Foreign Application Priority Data
Jun. 7, 2016 (JP) .................................. 2016-113144

(51) Int. Cl.
| | |
|---|---|
| *A61B 6/00* | (2006.01) |
| *G06K 9/00* | (2006.01) |
| *G03C 5/16* | (2006.01) |
| *G01T 1/24* | (2006.01) |

(52) U.S. Cl.
CPC .............. *A61B 6/482* (2013.01); *A61B 6/405* (2013.01); *A61B 6/42* (2013.01); *A61B 6/4241* (2013.01); *A61B 6/4283* (2013.01); *A61B 6/56* (2013.01); *G01T 1/247* (2013.01); *G03C 5/16* (2013.01); *G06K 9/0002* (2013.01); *A61B 6/488* (2013.01)

(58) Field of Classification Search
CPC ....... A61B 6/405; A61B 6/4241; A61B 6/482; A61B 6/42
USPC ......................................................... 358/471
See application file for complete search history.

(56) References Cited

U.S. PATENT DOCUMENTS

| | | | |
|---|---|---|---|
| 2013/0032696 A1* | 2/2013 | Tajima | ..................... A61B 6/42 250/208.1 |
| 2013/0259203 A1* | 10/2013 | Ishizaka | .................. H05G 1/64 378/98.2 |

FOREIGN PATENT DOCUMENTS

| | | |
|---|---|---|
| JP | 2012152477 A | 8/2012 |
| JP | 2013226332 A | 11/2013 |

* cited by examiner

*Primary Examiner* — Houshang Safaipour
(74) *Attorney, Agent, or Firm* — Cantor Colburn LLP

(57) ABSTRACT

A radiographic image capturing apparatus includes: scanning and signal lines; a two-dimensional array of detecting elements defining a detecting part; a control unit that reads image data from all detecting elements in a reading area of the detecting part by repeating a cycle of a readout process at N-line intervals, wherein the scanning line subjected to the readout process is shifted every cycle, where N is an integral number of at least 1; and a communication unit for external communication. The control unit detects a radiation emission start of a radiation irradiating apparatus, and if the readout process starts with an N+1th or any subsequent scanning line and then starts with any of first to N+1th scanning lines in a certain cycle, the control unit transfers the image data read in the certain cycle as preview image data substantially concurrently with the readout process.

9 Claims, 12 Drawing Sheets

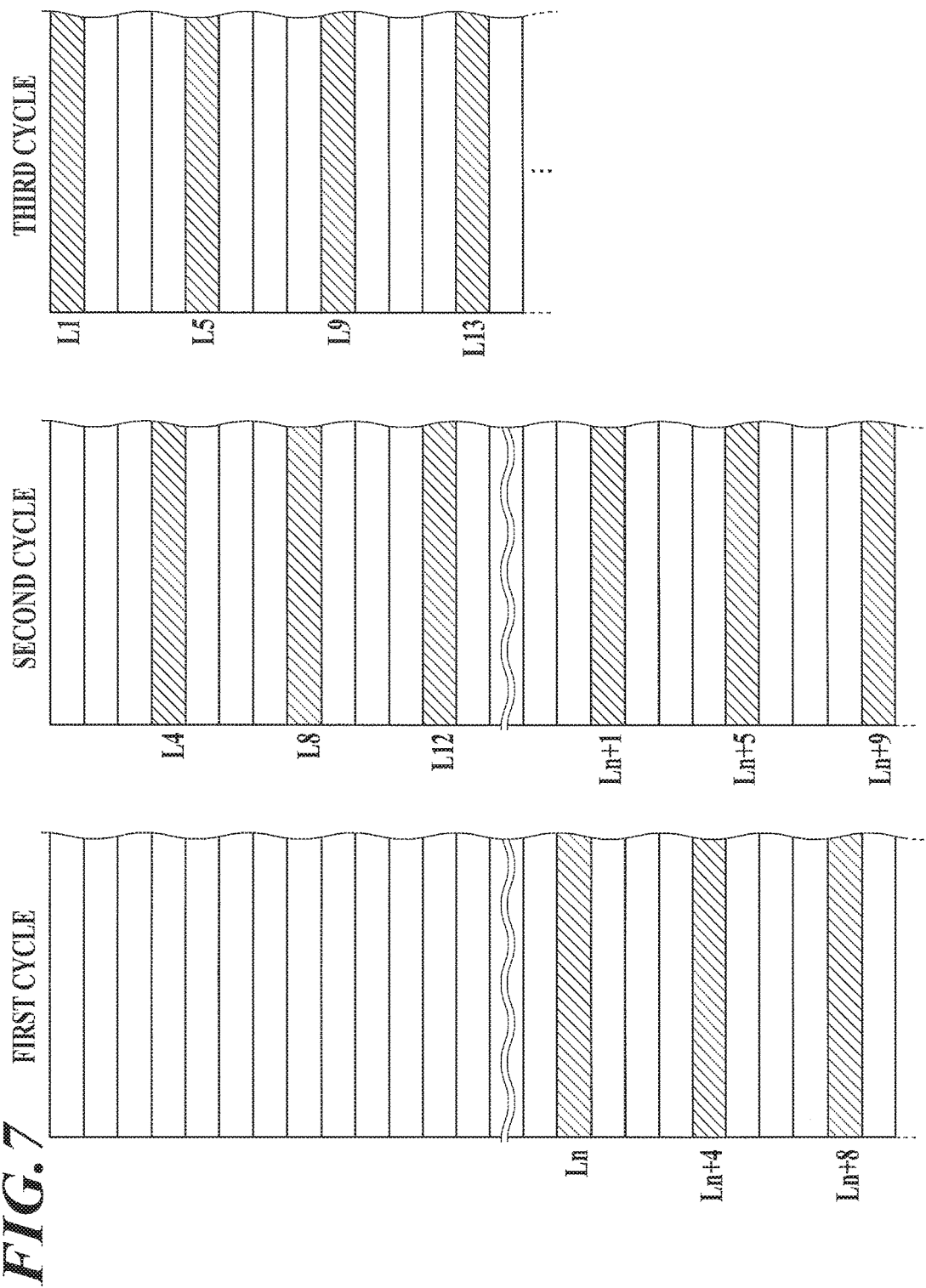

FIG. 9
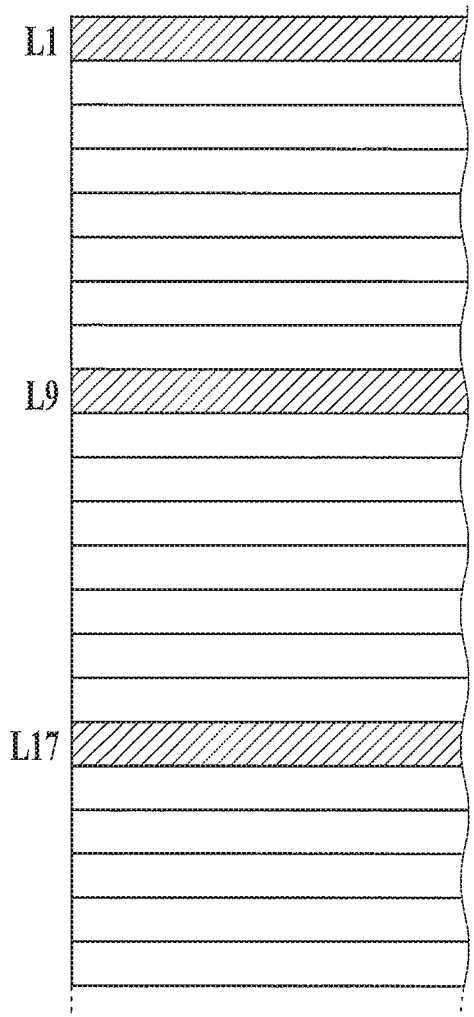
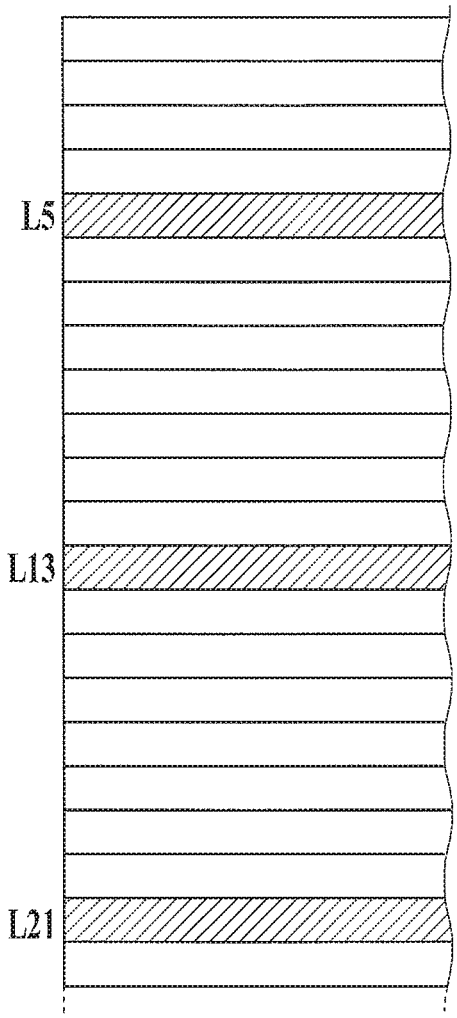

FIG.12

| | | | | | | |
|---|---|---|---|---|---|---|
| L1 | D(1,1) | D(1,2) | D(1,3) | D(1,4) | D(1,5) | |
| L2 | D(2,1) | D(2,2) | D(2,3) | D(2,4) | D(2,5) | |
| L3 | D(3,1) | D(3,2) | D(3,3) | D(3,4) | D(3,5) | |
| L4 | D(4,1) | D(4,2) | D(4,3) | D(4,4) | D(4,5) | |
| L5 | D(5,1) | D(5,2) | D(5,3) | D(5,4) | D(5,5) | |
| L6 | D(6,1) | D(6,2) | D(6,3) | D(6,4) | D(6,5) | |
| L7 | D(7,1) | D(7,2) | D(7,3) | D(7,4) | D(7,5) | |
| L8 | D(8,1) | D(8,2) | D(8,3) | D(8,4) | D(8,5) | |
| L9 | D(9,1) | D(9,2) | D(9,3) | D(9,4) | D(9,5) | |
| L10 | D(10,1) | D(10,2) | D(10,3) | D(10,4) | D(10,5) | |
| L11 | D(11,1) | D(11,2) | D(11,3) | D(11,4) | D(11,5) | |
| L12 | D(12,1) | D(12,2) | D(12,3) | D(12,4) | D(12,5) | |

FIG.13A
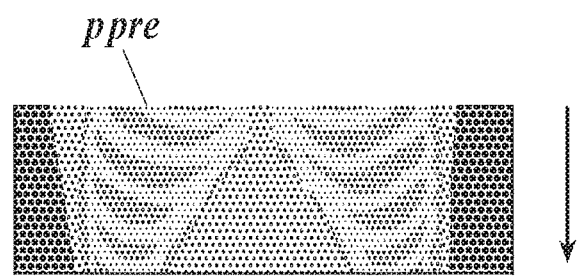
ppre
FIG.13B
ppre
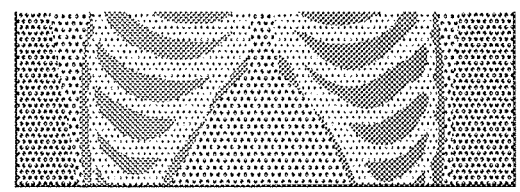

RADIOGRAPHIC IMAGE CAPTURING APPARATUS AND RADIOGRAPHIC IMAGE CAPTURING SYSTEM

CROSS-REFERENCE TO RELATED APPLICATIONS

The present invention claims priority under 35 U.S.C. § 119 to Japanese Application No. 2016-113144 filed on Jun. 7, 2016, the entirety of which is incorporated herein by references.

BACKGROUND OF THE INVENTION

Field of the Invention

The present invention relates to a radiographic image capturing apparatus and a radiographic image capturing system, in specific, a radiographic image capturing apparatus and a radiographic image capturing system which displays a preview image on a console.

Description of Related Art

Various radiographic image capturing apparatuses have been developed that generate electric charges in radiation detecting elements 7 (refer to FIG. 2 described below) in proportion to the dose of received radiation and read the generated electric charges as image data. The radiographic image capturing apparatuses of this type are known as flat panel detectors (FPDs). In contrast to traditional radiographic image capturing apparatuses of a dedicated (fixed) type integrated with a support table, radiographic image capturing apparatuses of a portable (cassette) type have recently been developed, where each apparatus includes a housing accommodating radiation detecting elements.

In image capturing, some radiographic image capturing apparatuses of a portable type cooperate with a radiation irradiating apparatus emitting radiation through mutual signal transmission (this scheme is hereinafter referred to as "cooperative scheme"). In this case, if a radiologist manipulates an exposure switch (refer to an exposure switch 56 in FIG. 3 or 4 described below) of the radiation irradiating apparatus to cause radiation emission, the radiation irradiating apparatus transmits radiation start signals to the radiographic image capturing apparatus.

With reference to FIG. 10, for example, the radiographic image capturing apparatus performs a resetting process of the radiation detecting elements 7 by causing a scan driving unit 15 (refer to FIG. 2 described below) to sequentially apply an ON voltage to scanning lines 5(L1) to 5(Lx) to remove electric charges remaining in the radiation detecting elements 7, during image capturing. Upon reception of the radiation start signals from the radiation irradiating apparatus as described above, the radiographic image capturing apparatus halts the resetting process of the radiation detecting elements 7 and causes the scan driving unit 15 to apply an OFF voltage to the scanning lines 5(L1) to 5(Lx), and thereby shifts the radiation detecting elements 7 to a charge accumulating mode.

The radiographic image capturing apparatus transmits interlock release signals to the radiation irradiating apparatus concurrently with the shift to the charge accumulating mode. Upon reception of the interlock release signals, the radiation irradiating apparatus starts irradiating the radiographic image capturing apparatus with radiation. In FIG. 10, the shaded portion represents the period of radiation emission. The radiographic image capturing apparatus then causes the scan driving unit 15 to sequentially apply an ON voltage to the scanning lines 5(L1) to 5(Lx) to read image data D from the radiation detecting elements 7.

Meanwhile, the above radiographic image capturing apparatus sometimes conducts image capturing without cooperation or mutual signal transmission with the radiation irradiating apparatus (this scheme is hereinafter referred to as "non-cooperative scheme").

In image capturing in the non-cooperative scheme, the radiographic image capturing apparatus autonomously detects the start of radiation emission from the radiation irradiating apparatus, in general. In the non-cooperative scheme, while waiting for the start of radiation emission from the radiation irradiating apparatus, the radiographic image capturing apparatus often performs the resetting process of the radiation detecting elements 7 (or the reading process of the image data D from the radiation detecting elements 7, also serving as the resetting process; the same shall apply to the following description) by causing the scan driving unit 15 to sequentially apply the ON voltage to the scanning lines 5(L1) to 5(Lx), as illustrated in FIG. 11, to prevent accumulation of dark charges (also called dark currents) in the radiation detecting elements 7, for example.

Upon detection of the start of radiation emission, the radiographic image capturing apparatus halts the resetting process of the radiation detecting elements 7 and causes the scan driving unit 15 to apply an OFF voltage to the scanning lines 5(L1) to 5(Lx) to shift to the charge accumulating mode. The radiographic image capturing apparatus then causes the scan driving unit 15 to sequentially apply an ON voltage to the scanning lines 5(L1) to 5(Lx) to read image data D from the radiation detecting elements 7.

In some cases, with reference to FIG. 11, the readout process for the image data D starts with application of an ON voltage to the scanning line 5 (the scanning line 5(L5) in FIG. 11) subsequent to the scanning line 5 (the scanning line 5(L4) in FIG. 11) to which an ON voltage has been applied at the end of the latest resetting process of the radiation detecting elements 7.

Meanwhile, a preview image can be displayed on a console to allow the radiologist to determine the need of recapturing of the image captured with the radiographic image capturing apparatus as explained above. In this case, for example, direct transfer of the image data D read at the radiographic image capturing apparatus as described above to the console takes a long time, thereby delaying the completion of display of the preview image on the console.

As a typical solution to this problem, a predetermined fraction of the image data D (hereinafter referred to as "preview image data Dpre" for a preview image) is extracted from the image data D read at the radiographic image capturing apparatus and transferred to the console. The console then generates a preview image based on the preview image data Dpre and displays the resulting preview image (e.g., refer to Japanese Patent Application Laid-Open Publication No. 2012-152477).

In detail, with reference to FIG. 12, the radiographic image capturing apparatus can extract the preview image data Dpre (for example, the shaded portions in FIG. 12) of the radiation detecting elements 7 connected to the scanning lines 5 at intervals of a predetermined number of lines (hereinafter referred to as "N-line intervals," where N is an integral number of at least 1; N is 3 in FIG. 12) from all the read image data D(n, m), and then transfer the preview image data Dpre to the console, where D(n, m) indicates image data read from the radiation detecting element 7(n, m)

in the line n and the column m among the radiation detecting elements 7 disposed in a two-dimensional array (e.g., refer to Japanese Patent Application Laid-Open Publication No. 2013-226332).

If this extraction of preview image data Dpre is applied to the image data D generated in image capturing in the non-cooperative scheme, the readout process for image data D starts with not the first scanning line 5(L1) but an intermediate scanning line 5(L) (the scanning line 5(L5) in FIG. 11) in the non-cooperative scheme, as illustrated in FIG. 11.

When the image data D (the preview image data Dpre) is read out from the radiation detecting elements 7 connected to the scanning lines 5 at N-line intervals from the image data D which has been read in the above-described way, and transferred to the console substantially concurrently with the readout process for the preview image data Dpre, the console generates and displays a preview image ppre in wipe transition starting from the middle to the lower end of the image (refer to FIG. 13A) and then restarting from the upper end (refer to FIG. 13B).

Unfortunately, this preview image ppre is not appropriate for observation. In addition, such a preview image ppre displayed in wipe transition starting from the middle of the image may bring the radiologist an uncomfortable feeling in observation.

SUMMARY OF THE INVENTION

An object of the invention, which has been accomplished to solve the above problems, is to provide a radiographic image capturing apparatus and a radiographic image capturing system capable of displaying a preview image ppre on a console in wipe transition starting from the upper end of the image, regardless of a cooperative scheme involving a readout process for image data D starting with the first scanning line 5(L1) or a non-cooperative scheme mostly involving a readout process for image data D starting with an intermediate scanning line 5(L).

To achieve the abovementioned objects, a radiographic image capturing apparatus reflecting one aspect of the present invention includes: a plurality of scanning lines; a plurality of signal lines; a two-dimensional array of a plurality of radiation detecting elements, the array defining a detecting part; a control unit that performs control to read image data from all the radiation detecting elements in a reading area of the detecting part by repeating a cycle of a readout process for reading image data at an interval of a number N of the scanning lines from one end side to the other end side of the reading area, wherein each of the scanning lines subjected to the readout process is shifted every cycle, where N is an integral number of at least 1; and a communication unit for external communication, wherein the control unit is configured to detect a start of radiation emission from a radiation irradiating apparatus, and if the readout process for the image data starts with an N+1th or any of the subsequent scanning lines from the one end side of the reading area and then starts with any of the first to N+1th scanning lines in a certain cycle, the control unit transfers, among the pieces of image data read in respective cycles, the image data read in the certain cycle as preview image data substantially concurrently with the readout process for the preview image data.

To achieve the abovementioned objects, a radiographic image capturing system reflecting one aspect of the present invention includes: a radiographic image capturing apparatus including: a plurality of scanning lines; a plurality of signal lines; a two-dimensional array of a plurality of radiation detecting elements, the array defining a detecting part; a control unit that performs control to read image data from all the radiation detecting elements in a reading area of the detecting part by repeating a cycle of a readout process for reading image data at an interval of a number N of the scanning lines from one end side to the other end side of the reading area, wherein each of the scanning lines subjected to the readout process is shifted every cycle, where N is an integral number of at least 1; and a communication unit for external communication; and a console that generates a preview image based on preview image data transferred from the radiographic image capturing apparatus and displays the preview image, wherein the control unit of the radiographic image capturing apparatus is configured to detect a start of radiation emission from a radiation irradiating apparatus, and transfers the image data to the console substantially concurrently with the readout process for the image data, and if the image data is read by firstly applying an ON voltage to any of the first to N+1th scanning lines from the one end side of the reading area in a certain cycle of the readout process at the radiographic image capturing apparatus, the console defines the image data read in the certain cycle as the preview image data among the pieces of image data read in respective cycles, and generates and displays the preview image based on the preview image data.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 7 illustrates application of an ON voltage starting with an intermediate scanning line (Ln) in the first cycle of a readout process in a non-cooperative scheme;

FIG. 9 illustrates example particular sequential application of an ON voltage to scanning lines in a readout process for image data;

FIG. 12 is a diagram for illustrating an example procedure of extracting preview image data from image data;

FIG. 13A illustrates a preview image displayed in wipe transition starting from the middle of the image; and FIG. 13B illustrates a preview image displayed in wipe transition restarting from the upper end of the image.

PREFERRED EMBODIMENT OF THE PRESENT INVENTION

Embodiments of a radiographic image capturing apparatus and a radiographic image capturing system will now be described with reference to the accompanying drawings.

Although the following description will focus on a radiographic image capturing apparatus of an indirect conversion type that includes a scintillator, converts received radiation into light having other wavelength (e.g., visible light) with the scintillator, and then converts the light into electrical signals with radiation detecting elements to thereby obtain image data, the invention may also be applied to a radiographic image capturing apparatus of a direct conversion type that directly detects radiation with radiation detecting elements without a scintillator.

[Radiographic Image Capturing Apparatus]

Figure 1:
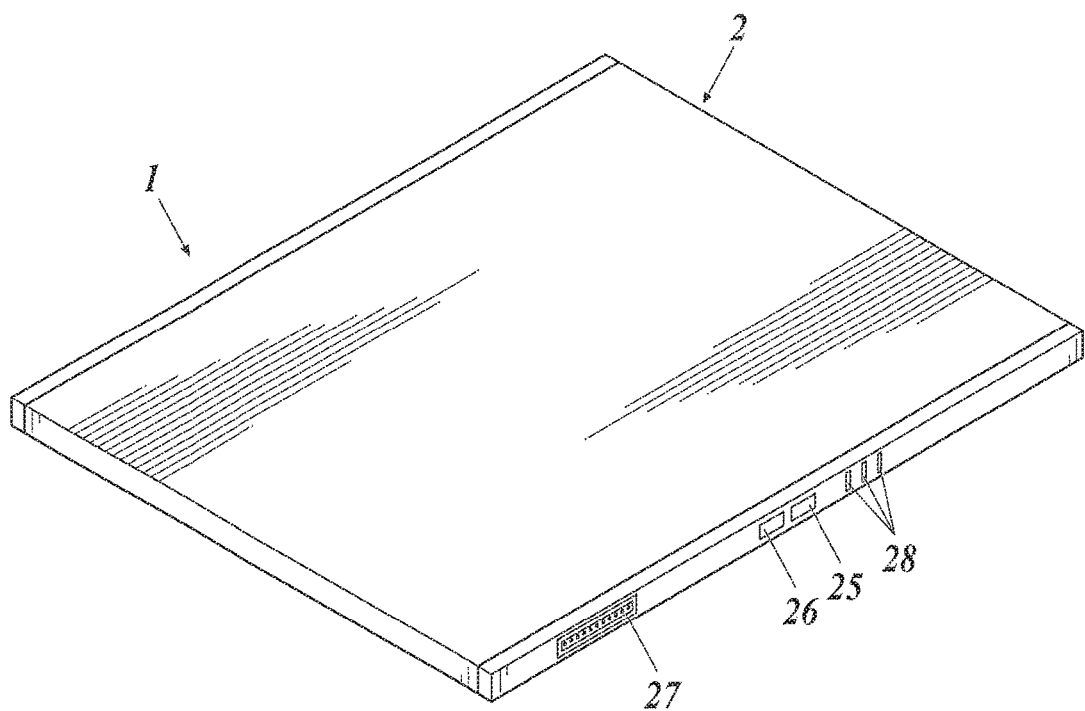
FIG. 1 is a perspective view of a radiographic image capturing apparatus according to an embodiment.
Figure 2:
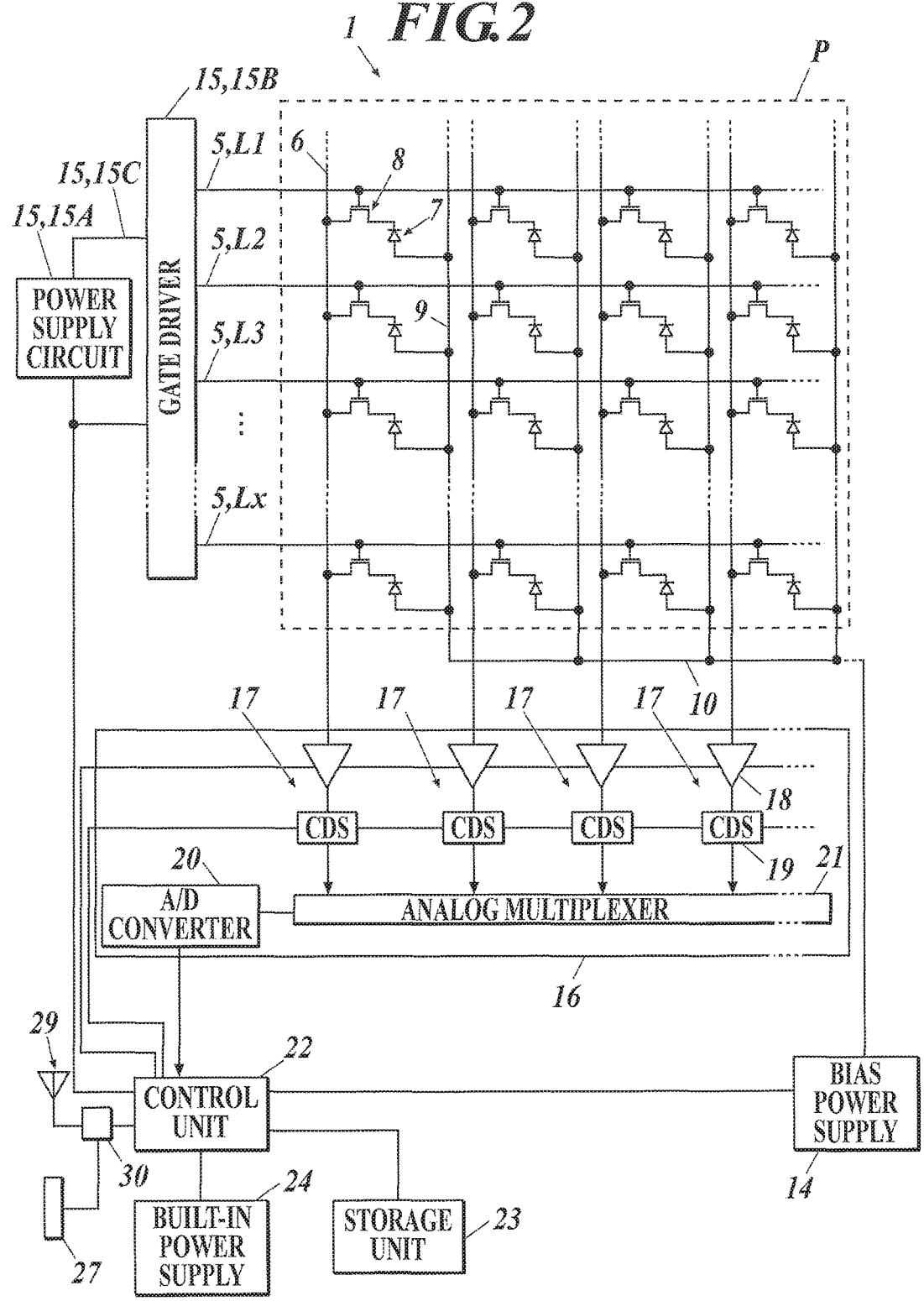
FIG. 2 is a block diagram illustrating an equivalent circuit of a radiographic image capturing apparatus.

FIG. 1 is a perspective view of a radiographic image capturing apparatus 1 according to an embodiment. FIG. 2 is a block diagram illustrating an equivalent circuit of the radiographic image capturing apparatus 1. The radiographic image capturing apparatus 1 includes a housing 2 (refer to FIG. 1) accommodating a sensor substrate (not shown) having a plurality of radiation detecting elements 7 (refer to FIG. 2) disposed in a two-dimensional array or matrix.

With reference to FIG. 1, one side face of the housing 2 of the radiographic image capturing apparatus 1 is provided with a power switch 25, a selector switch 26, a connector 27, and indicators 28. The opposite side face of the housing 2 is provided with an antenna 29 (not shown in FIG. 1; refer to FIG. 2 described below) for wireless communication with external devices.

With reference to FIG. 2, a two-dimensional array of the radiation detecting elements 7 defines a detecting part P in the embodiment. The radiation detecting elements 7 are connected to corresponding bias lines 9, where an inverse bias voltage is applied from a bias power supply 14 through a connecting line 10 and the bias lines 9 connected thereto. The radiation detecting elements 7 are also connected to respective thin film transistors (TFTs) 8 (functioning as switching elements). The TFTs 8 are connected to corresponding signal lines 6. The radiation detecting elements 7 generate electric charges therein in proportion to the dose of received radiation.

In a scan driving unit 15, an ON voltage and an OFF voltage are supplied from a power supply circuit 15A through a line 15C, switched by a gate driver 15B, and then applied to scanning lines 5(L1) to 5(Lx). The OFF voltage applied to each TFT 8 through the corresponding scanning line 5 turns off the TFT 8, resulting in disconnection between the corresponding radiation detecting element 7 and the corresponding signal line 6, to allow electric charges to be accumulated in the radiation detecting element 7. The ON voltage applied to each TFT 8 through the scanning line 5 turns on the TFT 8, to release the accumulated electric charges from the radiation detecting element 7 to the signal line 6.

The signal lines 6 are connected to respective readout circuits 17 contained in a readout IC 16. In the readout process for image data D, the gate driver 15B sequentially applies an ON voltage to the scanning lines 5(L1) to 5(Lx). The ON voltage turns on the TFTs 8, so that the electric charges flow from the radiation detecting elements 7 via the TFTs 8 and the signal lines 6 into the readout circuits 17 including amplifying circuits 18 and correlated double sampling circuits 19. The amplifying circuits 18 then output voltage values in proportion to the received electric charges.

The correlated double sampling circuits (indicated as "CDSs" in FIG. 2) 19 read the voltage values output from the amplifying circuits 18 as image data D of analog values and output the image data D. The output pieces of image data D are sequentially transmitted via an analog multiplexer 21 to an A/D converter 20. The A/D converter 20 then sequentially digitizes the analog image data D and sequentially stores the image data D of digital values into a storage unit 23.

The control unit 22 includes a computer provided with a central processing unit (CPU), read only memory (ROM), random access memory (RAM), and input/output interface (that are not shown), which are connected to each other with buses; or a field programmable gate array (FPGA). The control unit 22 may also be a dedicated circuit.

The control unit 22 is connected to the storage unit 23 including a static RAM (SRAM), a synchronous DRAM (SDRAM), or a NAND-type flash memory; and a built-in power source 24. The control unit 22 is also connected to a communication unit 30 for wired or wireless communication with external devices/apparatuses via the connector 27 or the antenna 29.

The control unit 22 controls the operation of the scan driving unit 15 to perform the resetting process of the radiation detecting elements 7, instructs the gate driver 15B of the scan driving unit 15 to apply an OFF voltage through the scanning lines 5(L1) to 5(Lx) to the TFTs 8 to cause the shift to a charge accumulating mode, and instructs the scan driving unit 15 and the readout circuits 17 to execute the readout process for reading image data D from the radiation detecting elements 7.

In the embodiment, the control unit 22 instructs the storage unit 23 to store part of the image data D read as explained above, and simultaneously instructs the communication unit 30 to transfer the part of the image data D by wired or wireless communication via the connector 27 or the antenna 29 to a console 58 (described below). The detail will be explained after the description of a radiographic image capturing system 100.

[Radiographic Image Capturing System]

A radiographic image capturing system 100 will now be described according to the embodiment. The radiographic image capturing system 100 can be installed in a radiographic room RA and a preparation room RB as illustrated in FIG. 3, or mounted on a mobile medical cart 70 as illustrated in FIG. 4, for example.

Figure 3:
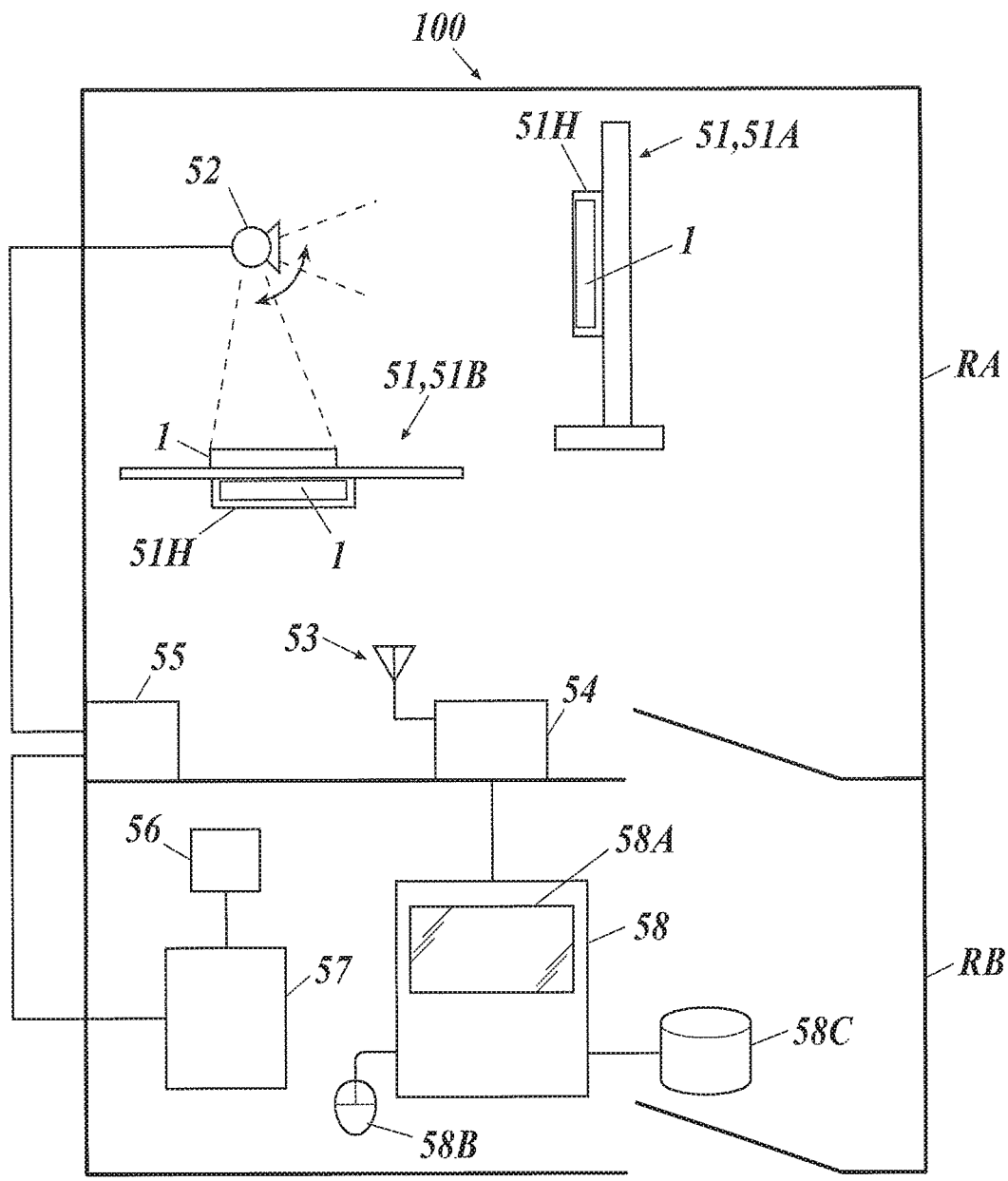
FIG. 3 illustrates an example configuration of a radiographic image capturing system according to the embodiment.
Figure 4:
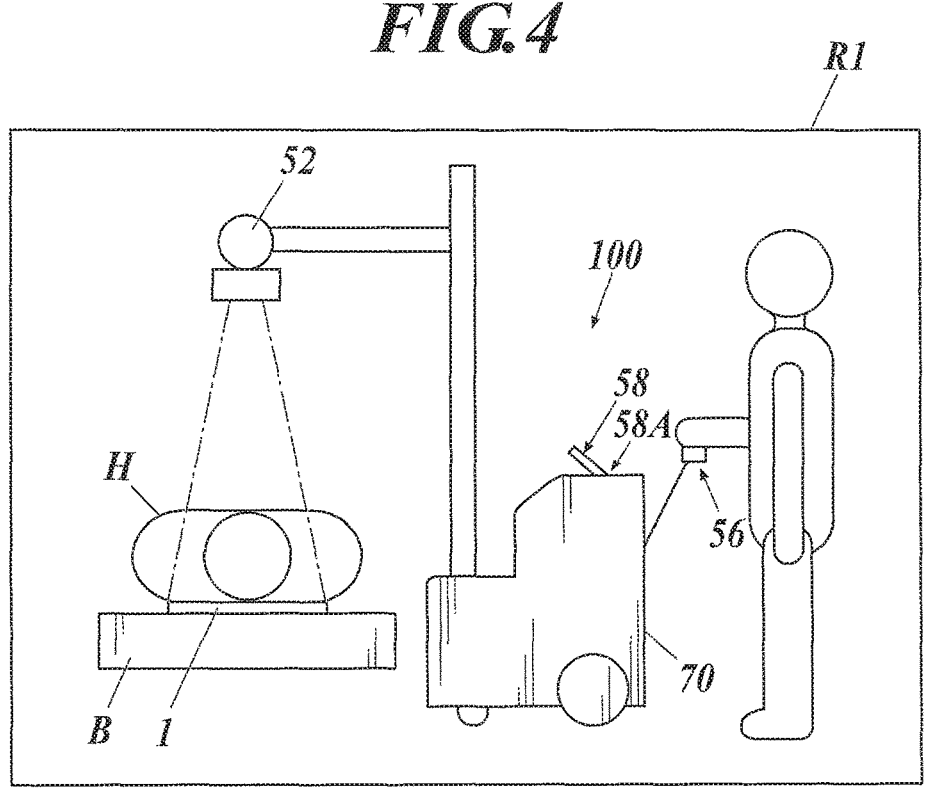
FIG. 4 illustrates another example configuration of a radiographic image capturing system according to the embodiment.

In the radiographic image capturing system 100 installed in the radiographic room RA as illustrated in FIG. 3, for example, the radiographic image capturing apparatus 1 is disposed in a cassette holder 51H of a radiography platform 51 (a radiography platform 51A for image capturing in an upright position or a radiography platform 51B for image capturing in a recumbent position) to be used in image capturing. Alternatively, the radiographic image capturing apparatus 1 may be disposed between the top board of the radiography platform 51B and a subject (not shown) lying on the top board, for example.

The radiographic room RA includes at least one radiation irradiating apparatus 52 for emitting radiation. The radiographic room RA is also provided with a relay 54 including an access point 53 for relaying wired or wireless communication among the devices/apparatuses inside and outside the radiographic room RA. The relay 54 relays the communication between the radiographic image capturing apparatus 1 and the console 58.

In image capturing in the cooperative scheme, the relay 54 may also be coupled to a generator 55 of the radiation irradiating apparatus 52 in addition to the console 58, to thereby achieve mutual signal transmission between the radiographic image capturing apparatus 1 and the generator 55 of the radiation irradiating apparatus 52 via the relay 54.

On the basis of the parameters, such as the tube voltage and current and the emission period (or mAs value), set by an operator (e.g., radiologist), the generator 55 of the radiation irradiating apparatus 52 conducts various controls over the radiation irradiating apparatus 52, for example, instructs the radiation irradiating apparatus 52 to emit radiation at a dose corresponding to the set parameters, such as the tube voltage.

The preparation room (also called an operator room) RB includes an operator station 57 of the radiation irradiating apparatus 52. The operator station 57 is equipped with an exposure switch 56, which the operator (e.g., radiologist) manipulates to instruct the generator 55 to start radiation emission, for example. The preparation room RB is also provided with the console 58 composed of a computer. Alternatively, the console 58 may be disposed outside the radiographic room RA or the preparation room RB or inside another room.

The console 58 is equipped with a display unit 58A composed of a cathode ray tube (CRT) display or a liquid crystal display (LCD), and connected to an input unit 58B, such as a mouse and/or a keyboard. The console 58 is connected to or includes a storage unit 58C composed of a hard disk drive (HDD).

Alternatively, with reference to FIG. 4, the radiographic image capturing system 100 including the radiation irradiating apparatus 52 and the console 58 may be mounted on the mobile medical cart 70, which is to be brought in a hospital ward R1 for image capturing, as described above. In this case, the generator 55 of the radiation irradiating apparatus 52 and the relay 54 (not shown in FIG. 4) are accommodated in the body of the mobile medical cart 70.

The radiographic image capturing apparatus 1 is disposed between a bed B and a subject H as illustrated in FIG. 4, or put on the body of a patient before image capturing. In response to manipulation of the operator (e.g., radiologist) on the exposure switch 56, the radiation irradiating apparatus 52 starts radiation emission for image capturing as in the above-described configuration.

Figure 5:
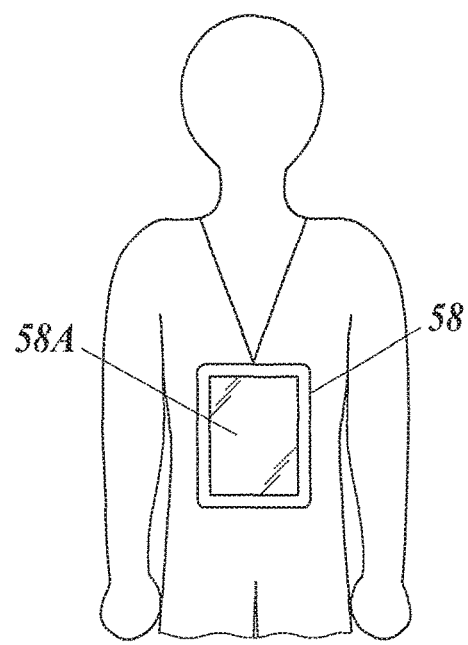
FIG. 5 illustrates an example configuration of a mobile console.

Although the console 58 is a desktop or laptop computer in FIG. 3 or 4, the console 58 may also be of a mobile type carried by the operator (e.g., radiologist) as illustrated in FIG. 5, for example.

[Detection of Start of Radiation Emission at Radiographic Image Capturing Apparatus]

In the embodiment, the radiographic image capturing apparatus 1 conducts image capturing in a non-cooperative scheme without mutual signal transmission with the radiation irradiating apparatus 52. The radiographic image capturing apparatus 1 is configured to autonomously detect the start of radiation emission from the radiation irradiating apparatus 52 (i.e., without receiving information on the start of radiation emission from the radiation irradiating apparatus 52).

The radiographic image capturing apparatus 1 can autonomously detect the start of radiation emission by various procedures, for example, based on an increase in current I flowing in the bias lines 9 and the connecting line 10 illustrated in FIG. 2 (refer to Japanese Patent Application Laid-Open Publication No. 2009-219538), an increase in electric charges leaking from the radiation detecting elements 7 via the TFTs 8 (refer to International Publication No. WO 2011/135917), or an increase in the value of image data D read from the radiation detecting elements 7 (refer to International Publication No. WO 2011/152093), which are caused by the start of radiation emission. See the cited references for the details.

[Readout Process and Transfer of Image Data at Radiographic Image Capturing Apparatus]

The readout process for image data D and the transfer of the image data D at the radiographic image capturing apparatus 1 will now be explained according to the embodiment. The operations of the radiographic image capturing apparatus 1 will also be explained according to the embodiment.

With reference to FIG. 12, the traditional apparatus extracts the image data D(n, m) of the radiation detecting elements 7(n, m) connected to the scanning lines 5 at N-line intervals (N is an integral number of at least 1; the same shall apply to the following explanation) from all the image data D(n, m) of the radiation detecting elements 7(n, m) stored in the storage unit 23. In this case, with reference to FIG. 11, for example, the readout process for the image data D involves sequential application of an ON voltage to all the scanning lines 5 while the target scanning lines 5 to receive the ON voltage are shifted one by one.

In contrast, the radiographic image capturing apparatus 1 according to the embodiment reads the image data D from part of the radiation detecting elements 7 connected to the scanning lines 5, i.e., from the radiation detecting elements 7 at N-line intervals, in the readout process for the image data D.

In detail, the control unit 22 (refer to FIG. 2) of the radiographic image capturing apparatus 1 controls the scan driving unit 15 and the readout circuits 17 to read image data D by sequentially applying an ON voltage to the scanning lines 5 at N-line intervals from one end side of the reading area of the detecting part P for reading the image data D to the other end side of the reading area in the embodiment, where the detecting part P is defined by the two-dimensional array of the radiation detecting elements 7. This process is repeated in the individual cycles while the target scanning lines 5 to receive the ON voltage are shifted, thereby achieving the readout process for reading the image data D from all the radiation detecting elements 7 in the reading area.

The reading area occupies the entire detecting part P, for the image data D to be read from all the radiation detecting elements 7 in the detecting part P. The reading area occupies part of the detecting part P encompassing part of the radiation detecting elements 7, for the image data D to be read from the part of the radiation detecting elements 7. In the following explanation, the image data D is read from all the radiation detecting elements 7 in the detecting part P.

Figure 6:
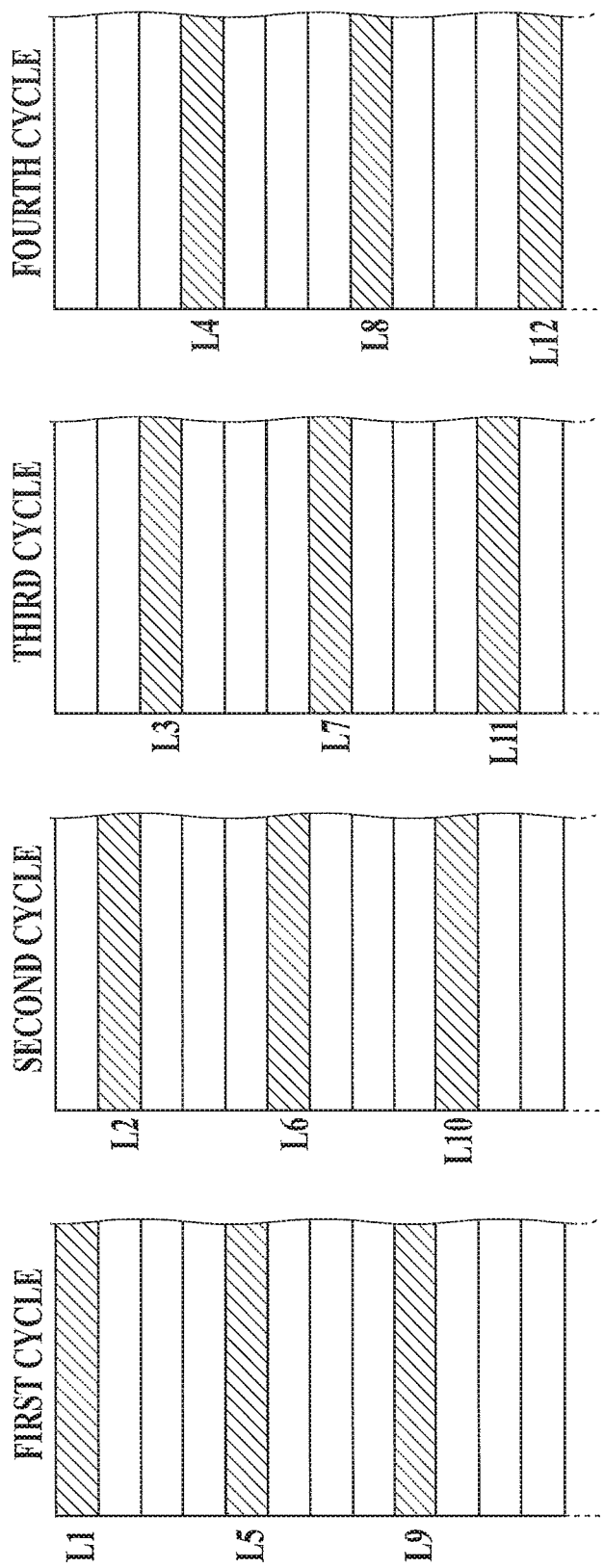
FIG. 6 illustrates sequential application of an ON voltage to scanning lines at three-line intervals in each cycle of a readout process for image data.

For example, with reference to FIG. 6, in a typical readout process for reading image data D from the radiation detecting elements 7 connected to the scanning lines 5 at three-line intervals in the embodiment, the control unit 22 sequentially applies an ON voltage to the scanning lines 5(L1), 5(L5), 5(L9), . . . in the first cycle; sequentially applies an ON voltage to the scanning lines 5(L2), 5(L6), 5(L10), . . . in the second cycle; sequentially applies an ON voltage to the scanning lines 5(L3), 5(L7), 5(L11), . . . in the third cycle;

and then sequentially applies an ON voltage to the scanning lines 5(L4), 5(L8), 5(L12), . . . in the fourth cycle. In FIG. 6, the shaded portions indicate the scanning lines 5(L) to receive the ON voltage in each cycle.

The resulting image data D read at intervals of N scanning lines 5 in each cycle is equivalent to the image data D extracted at N-line intervals from the stored image data D in each cycle (refer to FIG. 12). That is, the transfer of the image data D read in any cycle to the console 58 is equivalent to the transfer of the preview image data Dpre extracted from the stored image data D to the console 58 (refer to FIG. 12).

In the traditional image capturing illustrated in FIG. 12, the image data D read from all the radiation detecting elements 7 is temporarily stored into the storage unit 23, and the preview image data Dpre is then extracted from the stored image data D and transferred to the console 58, as explained above. In contrast, in the embodiment, the image data D is read and substantially simultaneously transferred as the preview image data Dpre to the console 58 in each cycle (the read image data D is also stored in the storage unit 23).

The preview image data Dpre can thus be transferred to the console 58 before completion of the readout process for reading the image data D from all the radiation detecting elements 7. This configuration can advance the time of generation and display of the preview image ppre at the console 58.

Figure 11:
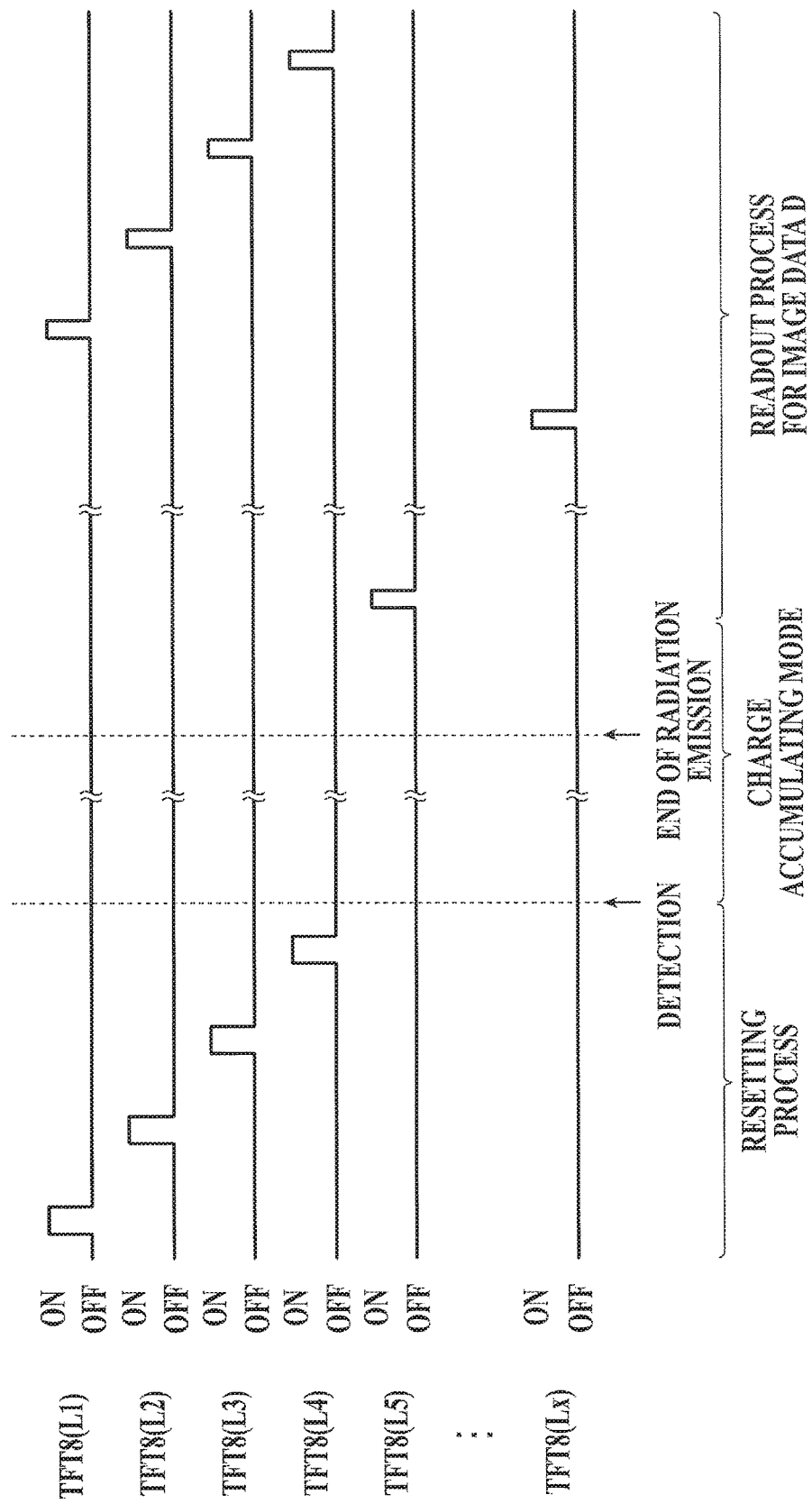
FIG. 11 is a timing chart for illustrating timings of application of an ON voltage to scanning lines in traditional image capturing in a non-cooperative scheme.

In general image capturing in the non-cooperative scheme in the embodiment illustrated in FIG. 7, the first cycle of the readout process for the image data D starts with application of an ON voltage to the intermediate scanning line 5(Ln), like the example illustrated in FIG. 11, although the first cycle of the readout process starts with the application of an ON voltage to the first scanning line 5(L1) in some cases (refer to FIG. 6).

If the image data D read by applying an ON voltage to the scanning lines 5 at N-line intervals as explained above is transferred to the console 58 in the first cycle, the preview image ppre may be displayed on the console 58 in wipe transition starting from the middle of the image, as illustrated in FIGS. 13A and 13B. This preview image ppre may bring the radiologist an uncomfortable feeling in observation.

In order to avoid this problem, the control unit 22 in the embodiment transfers the image data D read in a certain cycle of the readout process starting with application of an ON voltage to any of the first (i.e., the scanning line 5(L1)) to N+1th lines (i.e., the scanning line 5(L N+1)) from one end side (i.e., the end side adjacent to the scanning line 5(L1)) of the detecting part P as preview image data Dpre to the console 58 substantially concurrently with the readout process for the preview image data Dpre.

In specific, in the above-described example where N is 3 (i.e., N+1 is 4), among the pieces of image data D read in the respective cycles, the image data D read in a certain cycle of the readout process starting with the application of an ON voltage to any of the scanning lines 5(L1) to 5(L4) is transferred as the preview image data Dpre to the console 58 substantially concurrently with the readout process for the preview image data Dpre.

With reference to FIG. 7, if the first cycle of the readout process for the image data D starts with application of an ON voltage to the intermediate scanning line 5(Ln) (where n is larger than N+1) (i.e., in the above-described example, if the first cycle of the readout process starts with application of an ON voltage to any scanning line 5 other than the scanning lines 5(L1) to 5(L4)), the control unit 22 does not transfer the image data D read in the first cycle as the preview image data Dpre to the console 58.

In this case, the second cycle of the readout process for the image data D starts with application of an ON voltage to any of the scanning lines 5(L1) to 5(L4) (the scanning line 5(L4) in FIG. 7); hence, the control unit 22 transfers the image data D read in the second cycle as the preview image data Dpre to the console 58 substantially concurrently with the readout process for the preview image data Dpre.

If the first cycle of the readout process for the image data D starts with application of an ON voltage to any of the scanning lines 5(L1) to 5(L4) (as in the example illustrated in FIG. 6), the control unit 22 transfers the image data D read in the first cycle as the preview image data Dpre to the console 58 substantially concurrently with the readout process for the preview image data Dpre.

In response to reception of the preview image data Dpre from the radiographic image capturing apparatus 1 as explained above, the console 58 (refer to any of FIGS. 3 to 5) reads offset data o on the radiographic image capturing apparatus 1 preliminarily stored in the storage unit 58C, for example, and calculates preview image data Dpre* through correcting the preview image data Dpre for each radiation detecting element 7 of the radiographic image capturing apparatus 1 based on Expression (1):

$$D^* = D - o \quad (1)$$

The console 58 further provides simple image corrections to this corrected preview image data Dpre* and thereby generates a preview image ppre. The console 58 displays the preview image ppre in wipe transition on the display unit 58A after every generation of the preview image ppre. That is, every generation of the preview image ppre at the console 58, in response to sequential transfer of the preview image data Dpre read as explained above from the radiographic image capturing apparatus 1, causes the preview image ppre to be displayed in wipe transition on the display unit 58A.

This configuration allows the console 58 to display the preview image ppre in wipe transition starting from not the middle of the image (refer to FIGS. 13A and 13B) but the upper end of the image (refer to FIGS. 8A and 8B), in despite of the non-cooperative scheme where the readout process for the image data D often starts with the application of an ON voltage to the intermediate scanning line 5(Ln) as illustrated in FIG. 7.5

Advantageous Effects

As described above, the radiographic image capturing apparatus 1 according to the embodiment can appropriately display the preview image ppre in wipe transition from the upper end of the image on the console 58, in despite of the non-cooperative scheme where the readout process for the image data D often starts with the intermediate scanning line 5(Ln).

The radiologist does not feel uncomfortable in observation of this preview image ppre displayed in wipe transition and can accurately determine the need of recapturing of the image based on the preview image ppre.

In addition, the radiographic image capturing apparatus 1 according to the embodiment transfers the image data D (i.e., the preview image data Dpre) to the console 58 substantially concurrently with the readout process for the image data D (i.e., through streaming transfer) as explained above, unlike the traditional apparatus that reads all the image data D and then extracts the preview image data Dpre from the image data D. The console 58 can thus display the preview image ppre more rapidly than that in the traditional system.

[Image Capturing in Cooperative Scheme]

In the image capturing in the cooperative scheme, the radiographic image capturing apparatus 1 operates in synchronization with the radiation irradiating apparatus 52 through mutual signal transmission. In general, this radiographic image capturing apparatus 1 applies an ON voltage from not the intermediate scanning line 5(Ln) but the first scanning line 5(L1) in the readout process for the image data D.

The control unit 22 of the radiographic image capturing apparatus 1 transfers the image data D read in the first cycle (refer to the first cycle in FIG. 6) of the readout process for the image data D as the preview image data Dpre to the console 58 substantially concurrently with the readout process for the preview image data Dpre in the cooperative scheme.

Figure 8A:
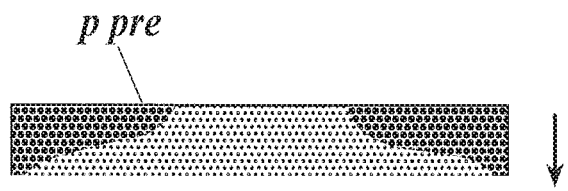
FIG. 8A illustrates a preview image displayed in wipe transition starting from the upper end of the image in the embodiment.
Figure 8B:
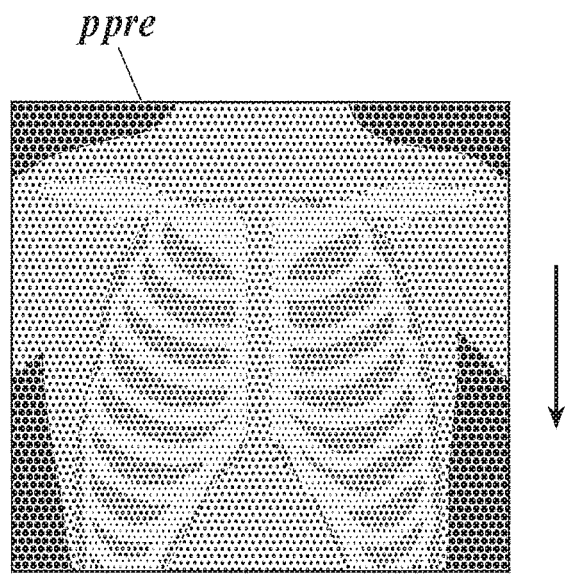
FIG. 8B illustrates a preview image displayed in wipe transition starting from the upper end of the image in the embodiment.

This preview image ppre can be appropriately displayed in wipe transition from the upper end of the image on the console 58 as illustrated in FIGS. 8A and 8B, in the cooperative scheme where the readout process for the image data D starts with the first scanning line 5(L1). The radiologist does not feel uncomfortable in observation of this preview image ppre displayed in wipe transition and can accurately determine the need of recapturing of the image based on the preview image ppre.

Figure 10:
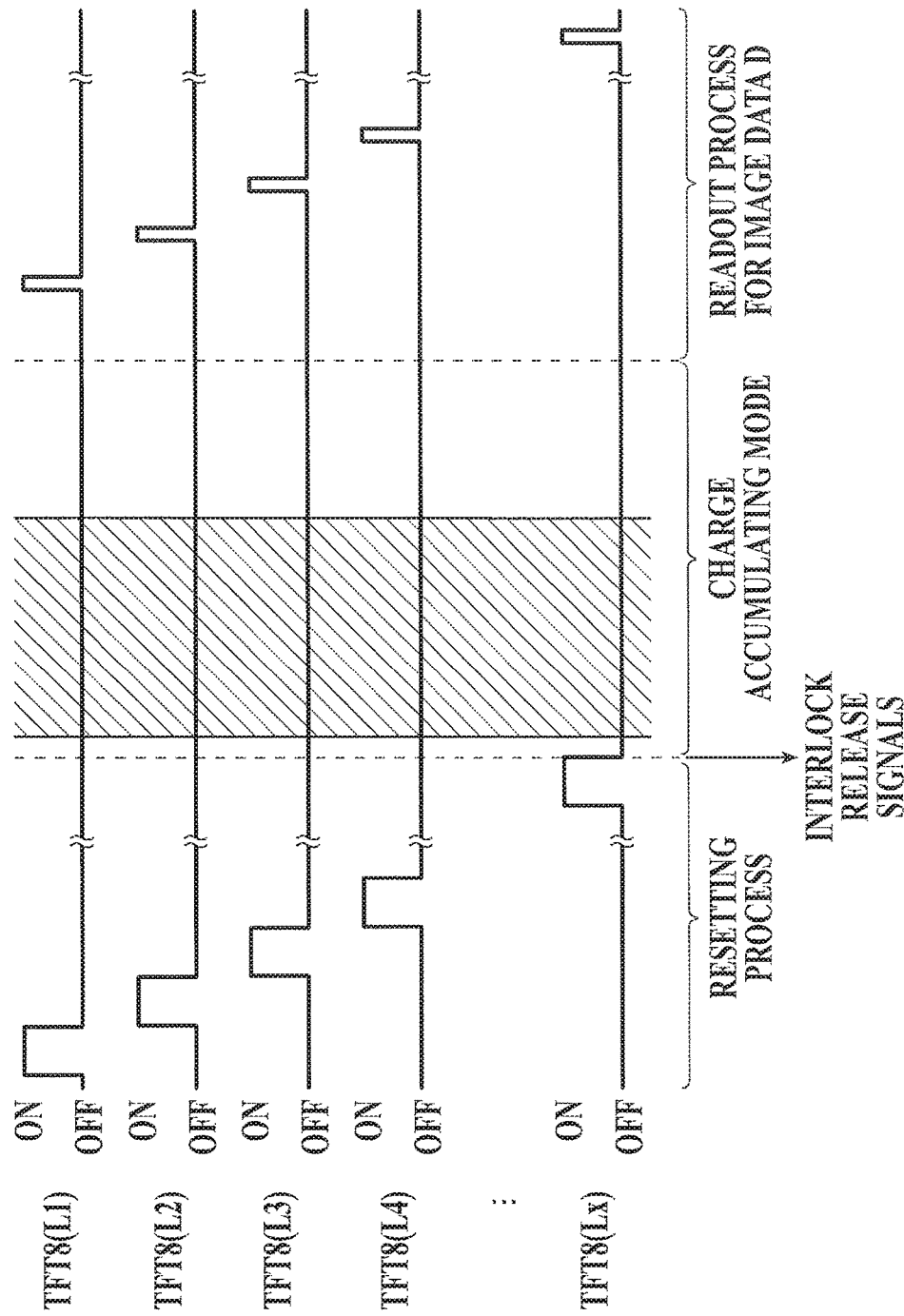
FIG. 10 is a timing chart for illustrating timings of application of an ON voltage to scanning lines in traditional image capturing in a cooperative scheme.

Also in this case, the radiographic image capturing apparatus 1 transfers the image data D (i.e., the preview image data Dpre) to the console 58 substantially concurrently with the readout process for the image data D (i.e., through streaming transfer) as explained above, unlike the traditional apparatus that reads all the image data D (refer to FIG. 10) and then extracts the preview image data Dpre from the image data D. The radiographic image capturing apparatus 1 can thus display the preview image ppre on the console 58 more rapidly than the traditional apparatus.

[Transfer of Corrected Preview Image Data from Radiographic Image Capturing Apparatus]

Although the console 58 corrects the received preview image data Dpre based on Expression (1) in the above-described embodiments, the radiographic image capturing apparatus 1 may alternatively correct the preview image data Dpre based on Expression (1) using the offset data o for each radiation detecting element 7, and then transfer the corrected preview image data Dpre* to the console 58.

The console 58 thus is not required to calculate the corrected preview image data Dpre*, resulting in reduced processing load on the console 58. In this case, the radiographic image capturing apparatus 1 preliminarily holds the offset data o for each radiation detecting element 7.

[Extraction of Image Data D Read in Multiple Cycles as Preview Image Data Dpre]

In the above-described embodiments, the image data D read in a single cycle (i.e., the second or first cycle in the non-cooperative scheme or the first cycle in the cooperative scheme) alone is transferred to the console 58 as the preview image data Dpre.

With reference to FIG. 9, for example, the second cycle of the readout process for the image data D at the radiographic image capturing apparatus 1 may involve particular application of an ON voltage. In detail, the second cycle of the readout process involves application of an ON voltage to a scanning line 5 at approximately the middle between two adjacent scanning lines 5 to which an ON voltage is applied in the first cycle. In this case, a preview image ppre generated based on the image data D read in the first cycle alone has low image quality. In order to generate a high-quality preview image ppre, use of the image data D read in the second cycle may be effective.

In order to meet this requirement, the control unit 22 of the radiographic image capturing apparatus 1 may transfer not only the image data D read in a certain cycle (i.e., the second or first cycle in the non-cooperative scheme or the first cycle in the cooperative scheme) but also the image data D read in each of the predetermined number of cycles subsequent to the certain cycle, as the preview image data Dpre, substantially concurrently with the readout process of the preview image data Dpre.

For example, with reference to FIG. 9, not only the image data D read in the first cycle but also the image data D read in the second cycle may be transferred as the preview image data Dpre substantially concurrently with the readout process of the preview image data Dpre.

The preview image ppre thus has sufficient image quality and allows the radiologist to accurately determine the need of recapturing of the image based on the preview image ppre.

[Transfer of Image Data D Other than Preview Image Data Dpre]

If the control unit 22 transfers the image data D read in the second cycle as the preview image data Dpre substantially concurrently with the readout process for the preview image data Dpre in the non-cooperative scheme, for example, the control unit 22 may temporarily store the image data D read in the first cycle into the storage unit 23. After the transfer of the preview image data Dpre, the control unit 22 may transfer the image data D read in the first cycle and the other image data D (i.e., the image data D read in the third and following cycles) to the console 58.

The console 58 displays the preview image ppre as described above, and then generates a radiographic image through precise image processing, such as gain correction, offset correction, and gradation processing depending on the portion to be imaged, of the preview image data Dpre and the image data D other than the preview image data Dpre. The generated radiographic image is subjected to any other known process, such as confirmation process (which is not described herein).

[Selection of Preview Image Data Dpre at Console]

In the above-described embodiments, the control unit 22 of the radiographic image capturing apparatus 1 selects the image data D read in any cycle as the preview image data Dpre among the image data D read in all the cycles, and transfers the selected image data D as the preview image data Dpre to the console 58 substantially concurrently with the readout process for the preview image data Dpre.

Alternatively, the radiographic image capturing system 100 may be configured such that the radiographic image capturing apparatus 1 directly transfers the image data D read out in the respective cycles simultaneously with the read out process for the image data D, and the console 58 selects the preview image data Dpre from among the pieces of the transferred image data D.

The console 58 may select the image data D read in any cycle as the preview image data Dpre from among the entire image data D transferred from the radiographic image capturing apparatus 1 in the same manner as the control unit 22 of the radiographic image capturing apparatus 1 selects the preview image data Dpre from the image data D read in the respective cycles.

In this case, the console 58 does not have information indicating which scanning line 5(L) corresponds to the start of the first cycle of the readout process at the radiographic image capturing apparatus 1; hence, this information is transmitted from the radiographic image capturing apparatus 1 to the console 58 concurrently with the transfer of the image data D.

The console 58 generates a preview image ppre based on the selected preview image data Dpre as described above, and displays the generated preview image ppre on the display unit 58A in wipe transition from the upper end of the image, as illustrated in FIGS. 8A and 8B.

The radiologist does not feel uncomfortable in observation of this preview image ppre displayed in wipe transition and can accurately determine the need of recapturing of the image based on the preview image ppre. In addition, the preview image ppre can be generated substantially simultaneously with the transfer of the preview image data Dpre from the radiographic image capturing apparatus 1, and can thus be displayed on the console 58 more rapidly than that in the traditional system.

In this case, the console 58 temporarily stores the remainder, i.e., the image data D other than the preview image data Dpre, into the storage unit 58C. After the above-described generation and display of the preview image ppre, the console 58 reads the remainder or the remaining image data D from the storage unit 58C, and generates a radiographic image through precise image processing, such as gain correction, offset correction, and gradation processing depending on the portion to be imaged, of the preview image data Dpre and the remainder or the remaining image data D.

The above-described embodiments should not be construed to limit the invention and may be appropriately modified within the gist of the invention.

What is claimed is:

1. A radiographic image capturing apparatus comprising:
    a plurality of scanning lines;
    a plurality of signal lines;
    a two-dimensional array of a plurality of radiation detecting elements, the array defining a detecting part;
    a control unit that performs control to read image data from all the radiation detecting elements in a reading area of the detecting part by repeating a cycle of a readout process for reading image data at an interval of a number N of the scanning lines from one end side to the other end side of the reading area, wherein each of the scanning lines subjected to the readout process is shifted every cycle, where N is an integral number of at least 1; and
    a communication unit for external communication, wherein
    the control unit is configured to detect a start of radiation emission from a radiation irradiating apparatus, and
    if the readout process for the image data starts with an N+1th or any of the subsequent scanning lines from the one end side of the reading area and then starts with any of the first to N+1th scanning lines in a certain cycle, the control unit transfers, among the pieces of image data read in respective cycles, the image data read in the certain cycle as preview image data;
    wherein if an ON voltage is firstly applied to any of the first to N+1th scanning lines from the one end side of the reading area in the readout process for the image data, the control unit transfers the image data read in the first cycle as the preview image data, and
    if an ON voltage is firstly applied to any scanning line other than the first to N+1th scanning lines from the one end side of the reading area in the readout process for the image data, the control unit transfers the image data read in the second cycle of the readout process as the preview image data.

2. The radiographic image capturing apparatus of claim 1, further comprising:
    a scan driving unit that switches a voltage to be applied to each of the scanning lines between an ON voltage and an OFF voltage; and
    one or more switching elements connected to the respective scanning lines, the switching elements each allowing each of the radiation detecting elements to accumulate one or more electric charges in response to application of the OFF voltage and to release the accumulated electric charges to each of the signal lines in response to application of the ON voltage, wherein
    the control unit performs the control to read the image data from all the radiation detecting elements in the reading area of the detecting part defined by the two-dimensional array of the radiation detecting elements by repeating the cycle of the readout process by sequentially applying the ON voltage to the scanning lines at the interval of the number N of the scanning lines from the one end side to the other end side of the reading area, wherein each of the scanning lines to receive the ON voltage is shifted every cycle, where N is an integral number of at least 1.

3. The radiographic image capturing apparatus of claim 1, wherein if the image data read in the second cycle is transferred as the preview image data the control unit stores the image data read in the first cycle into a storage unit, and after transferring the preview image data, transfers the image data read in the first cycle together with other image data.

4. The radiographic image capturing apparatus of claim 1, wherein
    the control unit is configured to perform image capturing in cooperation with the radiation irradiating apparatus, and
    the control unit transfers the image data read in the first cycle of the readout process as the preview image data.

5. The radiographic image capturing apparatus of claim 1, wherein the control unit also transfers image data read in each of a predetermined number of cycles subsequent to the certain cycle as the preview image data.

6. The radiographic image capturing apparatus of claim 1, wherein in the transferring process of the preview image data, the control unit transfers corrected preview image data obtained by subtracting offset data from the preview image data.

7. A radiographic image capturing system comprising:
    a radiographic image capturing apparatus including:
        a plurality of scanning lines;
        a plurality of signal lines;
        a two-dimensional array of a plurality of radiation detecting elements, the array defining a detecting part;
        a control unit that performs control to read image data from all the radiation detecting elements in a reading area of the detecting part by repeating a cycle of a readout process for reading image data at an interval of a number N of the scanning lines from one end side to the other end side of the reading area, wherein each of the scanning lines subjected to the readout process is shifted every cycle, where N is an integral number of at least 1; and
        a communication unit for external communication; and a console that generates a preview image based on preview image data transferred from the radiographic image capturing apparatus and displays the preview image, wherein the control unit of the radiographic image capturing apparatus is configured to detect a start of radiation emission from a radiation irradiating apparatus, and transfers the image data to the console substantially concurrently with the readout process for the image data, and if the image data is read by firstly applying an ON voltage to any of the first to N+1th scanning lines from the one end side of the reading area in a certain cycle of the readout process at the radiographic image capturing apparatus, the console defines the image data read in the certain cycle as the preview image data among the pieces of image data read in respective cycles, and generates and displays the preview image based on the preview image data;

wherein if an ON voltage is firstly applied to any of the first to N+1th scanning lines from the one end side of the reading area in the readout process for the image data, the control unit transfers the image data read in the first cycle as the preview image data, and if an ON voltage is firstly applied to any scanning line other than the first to N+1th scanning lines from the one end side of the reading area in the readout process for the image data, the control unit transfers the image data read in the second cycle of the readout process as the preview image data.

8. The radiographic image capturing system of claim 7, wherein the console generates and displays the preview image, and also generates a radiographic image based on the preview image data and a remainder of the image data.

9. The radiographic image capturing apparatus of claim 1, wherein the image data read as the preview image data is transferred before completion of the readout process for the image data from all the radiation detecting elements.

\* \* \* \* \*